United States Patent [19]

Boozalis et al.

[11] 4,168,210
[45] Sep. 18, 1979

[54] METHOD OF REDUCING REACTION BETWEEN HYDROGEN HALIDES AND OLEFINICALLY UNSATURATED COMPOUNDS

[75] Inventors: Theodore S. Boozalis; John B. Ivy, both of Lake Jackson, Tex.

[73] Assignee: The Dow Chemical Company, Midland, Mich.

[21] Appl. No.: 781,229

[22] Filed: Mar. 25, 1977

[51] Int. Cl.$^2$ .......................... B01D 3/34; C07C 7/18
[52] U.S. Cl. ......................................... 203/6; 203/38; 203/62; 260/654 H; 260/652.5 R; 260/654 S; 423/488; 585/3; 585/952
[58] Field of Search ................... 260/652.5 R, 652 P, 260/677 A, 666.5, 654 S, 654 H; 203/6-9, 38, 62, 54, 86; 423/488

[56] References Cited

U.S. PATENT DOCUMENTS

| | | | |
|---|---|---|---|
| 2,376,075 | 5/1945 | Morris | 260/652.5 |
| 2,517,895 | 8/1950 | Larchar | 260/652.5 |
| 2,615,791 | 10/1952 | Raley | 203/6 |
| 2,628,934 | 2/1953 | Raley et al. | 203/6 |
| 2,719,181 | 9/1955 | Cole | 260/652.5 |
| 3,976,705 | 8/1976 | Lukes et al. | 260/654 S |

*Primary Examiner*—Wilbur L. Bascomb, Jr.
*Attorney, Agent, or Firm*—A. C. Ancona

[57] ABSTRACT

A method for reducing losses due to reactions between hydrogen halides and olefinically unsaturated organic compounds in the presence of transition metals which act as catalysts for hydrohalogenation in mixtures containing same by adding to said mixtures a compound selected from the class consisting of alkyl diketones. The present invention is of particular value in the separation of components of said mixtures by distillation, but may also be usefully employed in any operation in which these mixtures are maintained in the presence of said catalytic materials. The present method offers advantages over the prior art because of the relative low toxicity and flammability of diketones and the fact that no undesirable solids are formed to foul process equipment as with some known methods.

5 Claims, No Drawings

METHOD OF REDUCING REACTION BETWEEN HYDROGEN HALIDES AND OLEFINICALLY UNSATURATED COMPOUNDS

BACKGROUND OF THE INVENTION

The addition of hydrogen halides to olefinically unsaturated organic compounds is well known to the art. It is also well known that these reactions are catalyzed by metals such as, for example, iron, cobalt, chromium, and nickel which are components of most pipes, processing equipment and storage tanks. Mixtures containing a hydrogen halide and one or more olefinically unsaturated organic compounds are commonly produced in large volume as by-products in a wide variety of industrial halogenation processes. Representative processes of this character are those involving halo-substitution of olefins or other unsaturated compounds with the concomitant formation of hydrogen halide, as well as those wherein the hydrogen halide is itself reacted with the unsaturated organic compound. These mixtures are seldom discarded since their components are valuable raw materials which are either recycled to the reactor or used in other chemical processes involving halogenated hydrocarbons.

A wide variety of compounds is known to the are to prevent hydrohalogenation reactions catalyzed by aluminum halides. These aluminum salts, due to their extreme reactivity, readily interact with and are destroyed by virtually any organic compound that contains a functional group. For example, U.S. Pat. No. 3,976,705 teaches the use of such diverse compounds as alcohols, aldehydes, organic acids, nitro-organic compounds, ketones, alkoxides, ammonia and hydrazine and additionally amines, amides, nitriles, thiols, sulfonic acids, phenols, esters, glycols and the like for preventing undesirable aluminum halide catalyzed hydrohalogenations. Aluminum halides also rapidly interact with a vast number of inorganic compounds. Since aluminum reacts, often violently, with and is severely corroded by hydrogen chloride and chlorinated hydrocarbons, even at low temperatures, it is not suitable as a metal for construction of processing equipment such as tanks, stills, heat exchangers, etc. which are exposed to these materials.

Process equipment designed for exposure to hydrogen chloride and/or chlorinated hydrocarbons is commonly fabricated from materials containing metals of the first transition series of the periodic chart, i.e., titanium, vanadium, chromium, manganese, iron, cobalt, nickel and copper. Numerous of methods are known to the art for reducing losses attributable to catalytically-induced interactions normally encountered when mixtures of hydrogen halide and olefinically unsaturated organic compounds are distilled, stored, transported, or otherwise maintained in the presence of metals of the first transition series.

In one such method the mixture is passed through water or an aqueous solution which selectively dissolves the hydrogen halide. While removal of the halide component of the mixture in this fashion is relatively simple, the step whereby anhydrous hydrogen halide is recovered from the aqueous wash solution is normally so expensive as to be economically unfeasible. In other separation methods the hydrogen halide is taken up by one or the other of a wide variety of chemicals in the form of a loose molecular adduct which is thereafter decomposed. This method, while expensive to operate due to high chemical and handling costs, is particularly effective when dealing with mixtures containing hydrogen fluoride, though it is not well adapted to the removal of the other hydrogen halides from such mixtures. The easiest method for separating the components of the mixture is by fractional distillation, the hydrogen halide usually coming off the top of the still and the unsaturated component being collected as bottoms. The drawback of this method is that whenever the separation is effected in metallic distillation columns, especially those made of a ferrous alloy, there ensues extensive hydrohalogenation of the unsaturated component of the mixture, it having been observed that this reaction is catalyzed by the salts which are formed in the column as the metal surfaces therein are attacked by acid. Even in the case of nickel-lined columns, considerable hydrohalogenation occurs once the liner has become so corroded as to give rise to the presence of appreciable amounts of nickel halide in the column.

In a somewhat different approach U.S. Pat. No. 2,615,791 discloses the use of nitriles and isonitriles to reduce the catalytically-induced reaction between hydrogen halides and olefinic compounds. While these nitriles and isonitriles are effective in controlling these reactions, they have several disadvantages in a practical application. They are highly toxic, making their handling both dangerous and expensive. They are also highly flammable and, when heated, emit toxic fumes. They can also react with steam to produce toxic vapors. A major process disadvantage of the nitriles and isonitriles is that they decompose under conditions of use to form solid hydrohalide salts. These solid salts can foul reboilers, heat exchangers, and other process equipment, resulting in expensive and time consuming plant shutdown.

BRIEF DESCRIPTION OF THE INVENTION

It is the object of the present invention to provide an efficient and economical method for reducing the reactions which occur between hydrogen halides and olefinically unsaturated organic compound when mixtures comprising these materials are processed or stored in the presence of certain metals which act as hydrohalogenation catalysts. In accordance with the present invention a small amount of a diketone is added to said mixtures to prevent the aforesaid undesirable reaction.

A wide variety of mixtures may be processed with reduced component-interaction according to the process of this invention. In addition to the hydrogen halide, whose concentration in the mixture may vary within wide limits, the mixture may contain any organic compound possessing one or more olefinic double bonds. Organic materials of this character which are commonly encountered in admixture with a hydrogen halide, and which may be separated therefrom in improved yield by practice of the present invention include alkenes, aralkenes and alicyclic compounds containing one or more olefinic linkages and embracing, besides the unsaturated hydrocarbons, their various substitution and addition products which contain at least one olefinic double bond. Representative unsaturated compounds frequently found in admixture with hydrogen halides are ethylene, propylene, 2-chloropropene, butenes, chlorobutenes, 3-methyl-1-butene, 2-methyl-2-butene, 3,3-dimethyl-1-butene, n-octene, 7-methyl-2-octene, cyclohexene, 1,3-butadiene, isoprene, piperylene, 2-ethyl-1,3-butadiene, 1,5-hexadiene, 3-phenyl-1-propene, and 1-phenyl-2-butene. These compounds may be present with the hydrogen halide either as individual compounds or as mixtures thereof. Further, the mixtures may include other materials such as paraffins and the undesired hydrohalogenation products themselves.

The diketones which are useful in suppressing the hydrohalogenation reaction in the above mixtures may be selected from the class of alkyl diketones having from 4 to 8 carbons, representative of which are for example, 2,3-butanedione, 2,3-pentanedione, 2,4-pentanedione, 2,3-hexanedione, 2,4-hexanedione, 2,5-hexanedione and 3,4-hexanedione as well as those diketones which contain substituents other than the two ketone groups providing, of course, the substituent groups are inert to the conditions of the reaction or do not in any way deleteriously affect the results desired. While these and other diketones are effective reaction suppresants when employed either singly or in combination with one another in the hydrogen halide-containing mixtures, the diketones containing five or less carbon atoms comprise a preferred class of additives for use in the present invention, representative members of this class being 2,3-butanedione, and 2,4-pentanedione.

The catalytically-induced hydrohalogenation occurring in the mixture can be greatly reduced by the addition of a diketone in even extremely small amount. Thus, it suffices to maintain a minimal diketone concentration in the mixture of only about 10 parts per million (ppm) based on the weight of the reactants present in the mixture, i.e., the olefinic compound and the hydrogen halide. It is preferred, however, that the diketone concentration in the liquid be from about 25 to 500 ppm. Larger amounts than this can be, and frequently are, used on occasion, but the reaction reducing effect of such larger amounts is not materially greater than that obtained when the diketone concentration falls within the preferred range.

The diketone may be added to a liquid mixture of the olefinic compound and the hydrogen halide in any manner. In the case of a batch operation, the requisite amount of diketone may be supplied in a single addition. On the other hand, when the mixture is subjected to processing in a continuous manner, as for example, a continuous distillation in a fractionating column, it is necessary that the diketone be added in a continuous or semi-continuous manner and in such a fashion as to distribute the same throughout all portions of the mixture, both liquid and vapor phases, in the system. In a continuous distillation, for example, such distribution is usually accomplished by adding the diketone near the top of the fractionating column, or at least well above the point of entry of the incoming feed stream.

While the addition of diketone proves effective in reducing catalytically-induced interaction between a hydrogen halide and any one or more of a variety of olefinically unsaturated compounds, the invention finds its widest employment in connection with mixtures essentially made up of hydrogen chloride and an olefinic hydrocarbon, of which propylene is a good example. Accordingly, the invention will be more particularly described hereinafter as it relates to the processing of hydrogen chloride-propylene mixtures.

DETAILED DESCRIPTION

EXAMPLE 1

A hydrogen chloride-propylene mixture containing approximately 45% propylene was passed through an iron vessel at a rate which allowed an average residence time in said vessel of about five minutes. The gaseous mixture was maintained at a temperature of about 100° C. and under a pressure of approximately 1.3 atmospheres. At a point just before the hydrogen chloride-propylene mixture entered the vessel, 2,4-pentanedione was added in a continuous manner at a rate which produced a concentration of 2,4-pentanedione of about 500 parts per million based on the weight of mixture entering the vessel. Before the addition of 2,4-pentanedione was begun, analysis of the effluent from the iron vessel showed an average loss of propylene due to isopropyl chloride formation of slightly more than 10%. When the 2,4-pentanedione was added to the hydrogen chloride-propylene mixture in the manner described above, propylene loss dropped sharply to about 3%, a reduction of approximately 70%.

The 2,4-pentanedione addition was stopped abruptly and acetonitrile (for comparison) was added to the mixture at the same point at which the 2,4-pentanedione had been added. No significant change in the rate of isopropyl chloride formation was detected upon switching to the nitrile.

The above comparison shows that the 2,4-pentanedione was at least as effective as the acetonitrile in reducing the hydrohalogenation of propylene while, as discussed above, yielding considerable advantages due to its lower toxicity, lower flammability and the fact that solid amine hydrochlorides will not form to cause plugging. The following examples show the results of using other diketones.

EXAMPLE 2

An approximately equal molar mixture of hydrogen chloride and propylene was fed to an empty tubular iron reactor. Iron is an active hydrohalogenation catalyst representative of the transition first series. The effluent from the iron reactor was analyzed for isopropyl chloride. Table I gives the percentage of the propylene converted to isopropyl chloride both before and after addition of various diketones. Similar conditions were employed for each diketone tested. This example shows the significant reduction in the amount of propylene hydrochlorination produced by the use of various diketones.

TABLE I

| | Percent Propylene Lost Due to Isopropyl Chloride Formation | |
| --- | --- | --- |
| Diketone Added | Before Diketone Addition | After Diketone Addition |
| 2,4-Pentanedione | 21.3 | 7.9 |
| 2,3-Butanedione | 21.8 | 9.9 |
| 2,5-Hexanedione | 27.8 | 6.5 |
| 2,4-Hexanedione | 21.9 | 8.8 |
| 2,3-Pentanedione | 19.2 | 7.7 |

We claim:

1. A method for reducing losses due to the hydrohalogenation reaction which occurs during the distillation of mixtures of hydrogen chloride and propylene in the presence of iron which comprises adding to said mixtures at least one compound of the group consisting of alkyl diketones having from 4 to 8 carbon atoms.

2. The method of claim 1 wherein the diketone is 2,3-butanedione.

3. The method of claim 1 wherein the diketone is 2,4-pentanedione.

4. The method of claim 1 wherein the diketone is employed at a concentration of at least about 10 parts per million based on the total weight of propylene and hydrogen chloride.

5. The method of claim 1 wherein the diketone is employed at a concentration of from about 25 to about 500 parts per million.